US011291977B2

(12) United States Patent
Deur-Bert et al.

(10) Patent No.: US 11,291,977 B2
(45) Date of Patent: Apr. 5, 2022

(54) ALPHA-ALUMINA-BASED CATALYST AND PROCESS FOR HYDROGENATION OF AN OLEFIN IN THE PRESENCE THEREOF

(71) Applicant: Arkema France, Colombes (FR)

(72) Inventors: Dominique Deur-Bert, Charly (FR); Dominique Garrait, Charly (FR); Laurent Wendlinger, Soucieu en Jarrest (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 16/620,913

(22) PCT Filed: Jun. 19, 2018

(86) PCT No.: PCT/EP2018/066162
§ 371 (c)(1),
(2) Date: Dec. 10, 2019

(87) PCT Pub. No.: WO2018/234261
PCT Pub. Date: Dec. 27, 2018

(65) Prior Publication Data
US 2020/0206720 A1 Jul. 2, 2020

(30) Foreign Application Priority Data
Jun. 20, 2017 (FR) ...................................... 1755585

(51) Int. Cl.
*B01J 23/44* (2006.01)
*B01J 21/04* (2006.01)
*B01J 35/10* (2006.01)
*C07C 17/354* (2006.01)

(52) U.S. Cl.
CPC .............. *B01J 23/44* (2013.01); *B01J 21/04* (2013.01); *B01J 35/1009* (2013.01); *C07C 17/354* (2013.01)

(58) Field of Classification Search
CPC ........ B01J 23/44; B01J 21/04; B01J 35/1009; C07C 17/354
See application file for complete search history.

(56) References Cited

U.S. PATENT DOCUMENTS

| | | | | |
|---|---|---|---|---|
| 2,995,510 A | * | 8/1961 | Bertolacini | .............. B01J 21/04 208/139 |
| 4,019,914 A | * | 4/1977 | Esper | ..................... C01F 7/442 501/127 |
| 5,015,614 A | * | 5/1991 | Baird, Jr | .................. B01J 21/04 502/250 |
| 5,710,317 A | * | 1/1998 | Oharu | ..................... C07C 69/63 560/227 |
| 5,710,353 A | * | 1/1998 | Shibanuma | ............ B01J 27/125 570/166 |
| 5,935,550 A | * | 8/1999 | Mohri | ....................... C01F 7/32 423/625 |
| 6,162,413 A | * | 12/2000 | Fujiwara | ................... C01F 7/02 423/625 |
| 6,303,091 B1 | * | 10/2001 | Mohri | ..................... C01B 13/14 423/263 |
| 6,476,281 B2 | * | 11/2002 | Qian | ....................... C07C 19/08 570/156 |
| 6,521,203 B1 | * | 2/2003 | Mohri | ....................... C01F 7/02 423/625 |
| 7,872,161 B2 | * | 1/2011 | Rao | .......................... C07C 17/23 570/156 |
| 8,912,370 B2 | * | 12/2014 | Devic | ...................... C07C 21/18 570/175 |
| 9,598,336 B2 | * | 3/2017 | Cheung | ................... C07C 21/18 |
| 9,856,192 B2 | * | 1/2018 | Lei | .......................... C07C 17/25 |
| 10,633,311 B2 | * | 4/2020 | Cheung | ............... B01J 35/1009 |
| 2010/0021374 A1 | * | 1/2010 | Mizuno | ..................... C01F 7/46 423/625 |
| 2010/0040535 A1 | * | 2/2010 | Azima | ...................... C01F 7/02 423/625 |
| 2011/0028770 A1 | * | 2/2011 | Wang | ...................... B01J 32/00 570/176 |
| 2012/0101314 A1 | * | 4/2012 | Devic | ................... C07C 17/354 570/175 |
| 2012/0101315 A1 | | 4/2012 | Devic | |
| 2013/0225882 A1 | * | 8/2013 | Wang | ...................... B01J 23/70 570/175 |

OTHER PUBLICATIONS

K. Nakane et al., 369 Analytica Chimica Acta, 79-85 (1998) (Year: 1998).*
K. Park et al., 35 Ind. Eng. Chem. Res., 4379-4385 (1996) (Year: 1996).*
E. Martin et al., 72 American Ceramic Society Bulletin, 71-77 (1993) (Year: 1993).*
M. Aramendia et al., 187 Journal of Catalysis, 392-399 (1999) (Year: 1999).*
E. Lopez et al., 62 Applied Catalysis B: Environmental, 57-65 (2006) (Year: 2006).*
F Habashi, Bull. Hist. Chem. 17/18 (1995) (Year: 1995).*
W. Suchanek et al., Journal of the American Ceramic Society, 399-412 (2010) (Year: 2010).*
A. Baba et al., Chemistry Africa, 1141-1145 (2020) (Year: 2020).*
M. Vlaskin et al., 54 High Temperature, 322-329 (2016) (Year: 2016).*
T. Zhao et al., 6 Materials Research Express (2019) (Year: 2019).*
Sumitomo Chemical (Product Databook) (downloaded Aug. 13, 2021) (Year: 2021).*

(Continued)

*Primary Examiner* — Alexander R Pagano

(74) *Attorney, Agent, or Firm* — NK Patent Law

(57) ABSTRACT

The present invention relates to a catalyst comprising a) from 90% to 99.99% by weight of alumina in which said alumina is at least 90% by weight α-alumina and b) from 0.01% to 10% by weight of at least one metal of valency 0 selected from the group consisting of Pd, Ru, Pt, Rh and Ir, characterized in that the chloride content of said catalyst is less than 500 ppm, based on the total weight of the catalyst.

7 Claims, No Drawings

(56) References Cited

OTHER PUBLICATIONS

S. Fujiwara et al., Sumitomo Kagaku (2007) (Year: 2007).*
ISA/EP; International Search Report and Written Opinion for International Patent Application No. PCT/EP2018/066162 fated Oct. 23, 2018, 10 pages.
Ertl, Gerhard et al., "Handbook of Heterogeneous Catalysis: Characterization of Solid Catalysts", WILEY-VCH Verlag GmbH & Co. KGaA, 2008, vol. 2, 2nd Edition, pp. 721-738.

* cited by examiner

ALPHA-ALUMINA-BASED CATALYST AND PROCESS FOR HYDROGENATION OF AN OLEFIN IN THE PRESENCE THEREOF

CROSS-REFERENCE TO RELATED APPLICATIONS

This application is a U.S. National Stage application of International Patent Application No. PCT/EP2018/066162, filed on Jun. 19, 2018, which claims the benefit of French Patent Application No. 1755585, filed on Jun. 20, 2017.

TECHNICAL FIELD OF THE INVENTION

The present invention relates to catalysts for the hydrogenation of olefins. In particular, the invention relates to supported catalysts for the hydrogenation of fluoroolefins.

TECHNOLOGICAL BACKGROUND OF THE INVENTION

The catalytic hydrogenation of fluoroolefins is frequently used in the production of hydrofluorocarbons. Various metals, such as Pd, supported on a substrate are known as hydrogenation catalysts, in particular in gas-phase reactions. Alumina is known as support for these catalysts. Alumina has different phases: $\alpha$, $\beta$, $\gamma$, $\delta$, $\theta$, $\eta$ or $\kappa$. Knunyants et al. (see Izv. Akad. Nauk. SSSR, (1960) 1412-1418) reports a catalyst Pd/[calcined $Al_2O_3$] used to catalyze the hydrogenation of $CF_3CF=CF_2$ (HFP) to give $CF_3CHFCHF_2$ (236ea) and $CF_3CF=CHF$ (1225ye) to $CF_3CHFCH_2F$ (245eb). The performance qualities of the catalyst can nevertheless be improved. There thus exists a need for novel hydrogenation catalysts which are stable and active.

SUMMARY OF THE INVENTION

According to a first aspect, the present invention provides a catalyst comprising a) from 90% to 99.99% by weight of alumina in which said alumina is at least 90% by weight $\alpha$-alumina and b) from 0.01% to 10% by weight of at least one metal of valency 0 selected from the group consisting of Pd, Ru, Pt, Rh and Ir, characterized in that the chloride content of said catalyst is less than 500 ppm, based on the total weight of the catalyst.

According to a preferred embodiment, the water content of said catalyst is less than 2% by weight, based on the total weight of the catalyst.

According to a preferred embodiment, the content by weight of carbon is less than 500 ppm, based on the total weight of the catalyst.

According to a preferred embodiment, the content by weight of sodium is less than 100 ppm, based on the total weight of the catalyst.

According to a preferred embodiment, the content by weight of antimony is less than 20 ppm, based on the total weight of the catalyst.

According to a preferred embodiment, in said catalyst:
the content by weight of gold is less than 100 ppm, based on the total weight of the catalyst, and/or
the content by weight of lead is less than 50 ppm, based on the total weight of the catalyst, and/or
the content by weight of zinc is less than 250 ppm, based on the total weight of the catalyst, and/or
the content by weight of iron is less than 50 ppm, based on the total weight of the catalyst, and/or
the content by weight of copper is less than 50 ppm, based on the total weight of the catalyst, and/or
the content by weight of magnesium is less than 50 ppm, based on the total weight of the catalyst, and/or
the content by weight of calcium is less than 50 ppm, based on the total weight of the catalyst, and/or
the content by weight of nickel is less than 50 ppm, based on the total weight of the catalyst, and/or
the content by weight of chromium is less than 10 ppm, based on the total weight of the catalyst, and/or
the content by weight of cobalt is less than 10 ppm, based on the total weight of the catalyst, and/or
the content by weight of manganese is less than 10 ppm, based on the total weight of the catalyst.

According to a second aspect, the present invention provides a process for the hydrogenation of an olefin comprising at least one fluorine atom which comprises bringing said olefin into contact with hydrogen in the gas phase in the presence of the catalyst according to the present invention, in order to form an alkane compound resulting from the hydrogenation of said olefin.

According to a preferred embodiment, said olefin is selected from the group consisting of 1,1,2,3,3,3-hexafluoropropene, 1,2,3,3,3-pentafluoropropene, 1,1,3,3,3-pentafluoropropene, 1,3,3,3-tetrafluoropropene, 2,3,3,3-tetrafluoropropene, 1,2-dichloro-3,3,3-trifluoropropene, 1-chloro-3,3,3-trifluoropropene and 2-chloro-3,3,3-trifluoropropene.

The present invention also provides a catalyst comprising a) from 90% to 99.99% by weight of alumina in which said alumina is at least 90% by weight $\alpha$-alumina and b) from 0.01% to 10% by weight of at least one metal of valency 0 selected from the group consisting of Pd, Ru, Pt, Rh and Ir, characterized in that the carbon content of said catalyst is less than 500 ppm, based on the total weight of the catalyst.

DETAILED DESCRIPTION OF THE INVENTION

According to a first aspect of the present invention, a catalyst is provided. Preferably, said catalyst comprises from 90% to 99.99% by weight of alumina and from 0.01% to 10% by weight of at least one metal of valency 0, based on the total weight of the catalyst.

According to a preferred embodiment, the alumina used is an alumina comprising at least 90% by weight of $\alpha$-alumina, based on the total weight of the alumina. Advantageously, the alumina used is an alumina comprising at least 91% by weight of $\alpha$-alumina, preferably at least 92% by weight, more preferentially at least 93% by weight, in particular at least 94% by weight, more particularly at least 95% by weight, favorably at least 96% by weight, more favorably at least 97% by weight, preferentially favorably at least 98% by weight, particularly favorably at least 99% by weight, of $\alpha$-alumina, based on the total weight of the alumina. According to a specific embodiment, the alumina consists of $\alpha$-alumina.

According to a preferred embodiment, said catalyst comprises at least 0.025% by weight of at least one metal of valency 0, advantageously at least 0.05% by weight, preferably at least 0.075% by weight, more preferentially at least 0.1% by weight, in particular at least 0.125% by weight, more particularly at least 0.15% by weight, favorably at least 0.175% by weight, of at least one metal of valency 0, based on the total weight of the catalyst.

According to a preferred embodiment, said catalyst comprises at most 10% by weight of at least one metal of valency 0, advantageously at most 9% by weight, preferably at most 8% by weight, more preferentially at most 7% by weight, in particular at most 6% by weight, more particularly at most 5% by weight, favorably at most 4% by weight, more favorably at most 3% by weight, particularly favorably at most 2% by weight, of at least one metal of valency 0, based on the total weight of the catalyst.

Thus, said catalyst can comprise at least 0.025% by weight of at least one metal of valency 0, advantageously at least 0.05% by weight, preferably at least 0.075% by weight, more preferentially at least 0.1% by weight, in particular at least 0.125% by weight, more particularly at least 0.15% by weight, favorably at least 0.175% by weight, of at least one metal of valency 0, and at most 10% by weight of at least one metal of valency 0, advantageously at most 9% by weight, preferably at most 8% by weight, more preferentially at most 7% by weight, in particular at most 6% by weight, more particularly at most 5% by weight, favorably at most 4% by weight, more favorably at most 3% by weight, particularly favorably at most 2% by weight, of at least one metal of valency 0, based on the total weight of the catalyst.

According to a specific embodiment, said catalyst can comprise at least 0.01% by weight or at least 0.0125% by weight or at least 0.015% by weight or at least 0.0175% by weight or at least 0.02% by weight or at least 0.0225% by weight or at least 0.025% by weight or at least 0.0275% by weight or at least 0.03% by weight or at least 0.0325% by weight or at least 0.035% by weight or at least 0.0375% by weight or at least 0.04% by weight or at least 0.0425% by weight or at least 0.045% by weight or at least 0.0475% by weight or at least 0.05% by weight or at least 0.0525% by weight or at least 0.055% by weight or at least 0.0575% by weight or at least 0.06% by weight or at least 0.0625% by weight or at least 0.065% by weight or at least 0.0675% by weight or at least 0.07% by weight or at least 0.0725% by weight or at least 0.075% by weight or at least 0.0775% by weight or at least 0.08% by weight or at least 0.0825% by weight or at least 0.085% by weight or at least 0.0875% by weight or at least 0.09% by weight or at least 0.0925% by weight or at least 0.095% by weight or at least 0.0975% by weight or at least 0.1% by weight or at least 0.125% by weight or at least 0.15% by weight or at least 0.175% by weight, of at least one metal of valency 0, based on the total weight of the catalyst.

According to a specific embodiment, said catalyst can comprise at most 10% by weight or at most 10% by weight or at most 9.5% by weight or at most 9% by weight or at most 8.5% by weight or at most 8% by weight or at most 7.5% by weight or at most 7% by weight or at most 6.5% by weight or at most 6% by weight or at most 5.5% by weight or at most 5% by weight or at most 4.5% by weight or at most 4% by weight or at most 3.5% by weight or at most 3% by weight or at most 2.5% by weight or at most 2% by weight, of at least one metal of valency 0, based on the total weight of the catalyst.

Thus, said catalyst can comprise at least 0.01% by weight or at least 0.0125% by weight or at least 0.015% by weight or at least 0.0175% by weight or at least 0.02% by weight or at least 0.0225% by weight or at least 0.025% by weight or at least 0.0275% by weight or at least 0.03% by weight or at least 0.0325% by weight or at least 0.035% by weight or at least 0.0375% by weight or at least 0.04% by weight or at least 0.0425% by weight or at least 0.045% by weight or at least 0.0475% by weight or at least 0.05% by weight or at least 0.0525% by weight or at least 0.055% by weight or at least 0.0575% by weight or at least 0.06% by weight or at least 0.0625% by weight or at least 0.065% by weight or at least 0.0675% by weight or at least 0.07% by weight or at least 0.0725% by weight or at least 0.075% by weight or at least 0.0775% by weight or at least 0.08% by weight or at least 0.0825% by weight or at least 0.085% by weight or at least 0.0875% by weight or at least 0.09% by weight or at least 0.0925% by weight or at least 0.095% by weight or at least 0.0975% by weight or at least 0.1% by weight or at least 0.125% by weight or at least 0.15% by weight or at least 0.175% by weight, of at least one metal of valency 0, and at most 10% by weight or at most 10% by weight or at most 9.5% by weight or at most 9% by weight or at most 8.5% by weight or at most 8% by weight or at most 7.5% by weight or at most 7% by weight or at most 6.5% by weight or at most 6% by weight or at most 5.5% by weight or at most 5% by weight or at most 4.5% by weight or at most 4% by weight or at most 3.5% by weight or at most 3% by weight or at most 2.5% by weight or at most 2% by weight, of at least one metal of valency 0, based on the total weight of the catalyst.

Preferably, said at least one metal of valency 0 is selected from the group consisting of Pd, Ru, Pt, Rh and Ir. Advantageously, said at least one metal of valency 0 is selected from the group consisting of Pd and Rh. Preferably, said at least one metal of valency 0 is palladium.

According to a specific embodiment, the carbon content of said catalyst is less than 900 ppm, based on the total weight of the catalyst, advantageously less than 800 ppm, preferably less than 700 ppm, more preferentially less than 600 ppm, in particular less than 500 ppm, more particularly less than 400 ppm, favorably less than 300 ppm, advantageously favorably less than 200 ppm, preferentially favorably less than 100 ppm, more preferentially favorably less than 50 ppm, particularly favorably less than 10 ppm, based on the total weight of the catalyst; more particularly favorably, said catalyst is devoid of carbon.

According to a preferred embodiment, the water content of said catalyst is less than 5% by weight, based on the total weight of the catalyst, advantageously less than 4% by weight, preferably less than 3% by weight, more preferentially less than 2% by weight, in particular less than 1% by weight, more particularly less than 0.5% by weight, favorably less than 0.1% by weight, more favorably less than 0.05% by weight, based on the total weight of the catalyst.

According to a preferred embodiment, the content by weight of chloride is less than 1000 ppm, based on the total weight of the catalyst, advantageously less than 900 ppm, preferably less than 800 ppm, more preferentially less than 700 ppm, in particular less than 600 ppm, more particularly less than 500 ppm, favorably less than 400 ppm, more favorably less than 300 ppm, advantageously favorably less than 200 ppm, preferentially favorably less than 100 ppm, based on the total weight of the catalyst.

According to a preferred embodiment, the content by weight of sodium is less than 1000 ppm, based on the total weight of the catalyst, advantageously less than 900 ppm, preferably less than 800 ppm, more preferentially less than 700 ppm, in particular less than 600 ppm, more particularly less than 500 ppm, favorably less than 400 ppm, more favorably less than 300 ppm, advantageously favorably less than 200 ppm, preferentially favorably less than 100 ppm, based on the total weight of the catalyst.

Preferably, when said at least one metal of valency 0 is selected from the group consisting of Pd, Ru, Pt, Rh and Ir, said catalyst can have:

a content by weight of gold is less than 100 ppm, preferably less than 50 ppm, based on the total weight of the catalyst, and/or a content by weight of lead is less than 50 ppm, preferably less than 25 ppm, based on the total weight of the catalyst, and/or a content by weight of zinc is less than 250 ppm, preferably less than 100 ppm, based on the total weight of the catalyst, and/or a content by weight of iron is less than 50 ppm, preferably less than 25 ppm, based on the total weight of the catalyst, and/or a content by weight of copper is less than 50 ppm, preferably less than 25 ppm, based on the total weight of the catalyst, and/or a content by weight of magnesium is less than 50 ppm, preferably less than 25 ppm, based on the total weight of the catalyst, and/or a content by weight of calcium is less than 50 ppm, preferably less than 25 ppm, based on the total weight of the catalyst, and/or a content by weight of nickel is less than 50 ppm, preferably less than 25 ppm, based on the total weight of the catalyst, and/or a content by weight of chromium is less than 10 ppm, based on the total weight of the catalyst, and/or a content by weight of cobalt is less than 10 ppm, based on the total weight of the catalyst, and/or a content by weight of manganese is less than 10 ppm, based on the total weight of the catalyst, and/or a content by weight of antimony is less than 20 ppm, preferably less than 10 ppm, based on the total weight of the catalyst.

In particular, when said at least one metal of valency 0 is palladium:

the content by weight of nickel is less than 100 ppm, more preferably less than 50 ppm, based on the total weight of the catalyst, and/or the content by weight of rhodium is less than 100 ppm, preferably less than 50 ppm, based on the total weight of the catalyst, and/or the content by weight of ruthenium is less than 100 ppm, preferably less than 50 ppm, based on the total weight of the catalyst, and/or the content by weight of iridium is less than 100 ppm, preferably less than 50 ppm, based on the total weight of the catalyst.

According to a preferred embodiment, the specific surface of said catalyst is between 0.1 and 150 m$^2$/g. Advantageously, the specific surface of said catalyst is between 0.3 and 140 m$^2$/g, preferably between 1 and 130 m$^2$/g, more preferentially between 2 and 120 m$^2$/g, more particularly between 3 and 110 m$^2$/g, favorably between 4 and 100 m$^2$/g.

Said catalyst can be obtained by mixing the different constituents of the latter in the proportions by weight shown.

According to a second aspect, the present invention provides a process for the hydrogenation of an olefin comprising at least one fluorine atom which comprises bringing said olefin into contact with hydrogen in the gas phase in the presence of the catalyst according to the present invention.

According to a preferred embodiment, said olefin is selected from the group consisting of 1,1,2,3,3,3-hexafluoropropene, 1,2,3,3,3-pentafluoropropene, 1,1,3,3,3-pentafluoropropene, 1,3,3,3-tetrafluoropropene, 2,3,3,3-tetrafluoropropene, 1,2-dichloro-3,3,3-trifluoropropene, 1-chloro-3,3,3-trifluoropropene and 2-chloro-3,3,3-trifluoropropene.

The hydrogenation stage can be carried out in the presence of a H$_2$/olefin molar ratio of between 1 and 40, preferably of between 2 and 15.

The hydrogenation stage can be carried out at a pressure of between 0.5 and 20 bara and preferably between 1 and 5 bara.

The catalyst can be present in any appropriate form, extrudates, pellets or beads.

The hydrogenation stage can be carried out under conditions such that the temperature at the inlet of the reactor is between 30° C. and 200° C., preferably between 40° C. and 140° C., and that at the outlet of the rector is between 50° C. and 250° C., preferably between 80° C. and 160° C.

The contact time (ratio of the catalyst volume to the total gas flow under standard temperature and pressure conditions) is advantageously between 0.1 and 60 seconds, preferably between 0.2 and 45 seconds, more preferentially between 0.2 and 30 seconds, in particular between 0.2 and 10 seconds and more particularly between 1 and 5 seconds.

Preferably, the reactor is an adiabatic reactor. This hydrogenation stage can be carried out in a multistage adiabatic reactor.

The present process makes possible the formation of an alkane compound resulting from the hydrogenation of the olefin comprising at least one fluorine atom, i.e. an alkane compound comprising at least one fluorine atom. Preferably, the present process makes possible the formation of a stream comprising the said alkane compound comprising at least one fluorine atom, the unreacted olefin and the unreacted hydrogen.

As mentioned above, the olefin can be 1,1,2,3,3,3-hexafluoropropene, 1,2,3,3,3-pentafluoropropene, 1,1,3,3,3-pentafluoropropene, 1,3,3,3-tetrafluoropropene, 2,3,3,3-tetrafluoropropene, 1,2-dichloro-3,3,3-trifluoropropene, 1-chloro-3,3,3-trifluoropropene or 2-chloro-3,3,3-trifluoropropene. Preferably, said alkane compound can be 1,1,1,2,3,3-hexafluoropropane, 1,1,1,2,3-pentafluoropropane, 1,1,1,3,3-pentafluoropropane, 1,1,1,3-tetrafluoropropane, 1,1,1,2-tetrafluoropropane, 2,3-dichloro-1,1,1-trifluoropropane, 3-chloro-1,1,1-trifluoropropane or 2-chloro-1,1,1-trifluoropropane.

Preferably, said process makes possible the hydrogenation of 1,1,2,3,3,3-hexafluoropropene to give 1,1,1,2,3,3-hexafluoropropane or the hydrogenation of 1,2,3,3,3-pentafluoropropene to give 1,1,1,2,3-pentafluoropropane or the hydrogenation of 1,1,3,3,3-pentafluoropropene to give 1,1,1,3,3-pentafluoropropane or the hydrogenation of 1,3,3,3-tetrafluoropropene to give 1,1,1,3-tetrafluoropropane or the hydrogenation of 2,3,3,3-tetrafluoropropene to give 1,1,1,2-tetrafluoropropane or the hydrogenation of 1,2-dichloro-3,3,3-trifluoropropene to give 2,3-dichloro-1,1,1-trifluoropropane or the hydrogenation of 1-chloro-3,3,3-trifluoropropene to give 3-chloro-1,1,1-trifluoropropane or the hydrogenation of 2-chloro-3,3,3-trifluoropropene to give 2-chloro-1,1,1-trifluoropropane.

The present process can be carried out continuously or batchwise.

The present process makes possible the complete or virtually complete conversion of the olefin used as starting material. Thus, the conversion of the olefin can be greater than 90%, advantageously greater than 91%, preferably greater than 92%, more preferentially greater than 93%, in particular greater than 94%, more particularly greater than 95%, favorably greater than 96%, more favorably greater than 97%, preferentially favorably greater than 98%, particularly favorably greater than 99%.

The present process makes possible the preparation of an alkane compound comprising at least one fluorine atom and resulting from said olefin comprising at least one fluorine atom with a very good selectivity. Advantageously, the selectivity for alkane compound comprising at least one fluorine atom and resulting from said olefin is greater than 98%, preferably greater than 98.5%, in particular greater than 99%.

Method of Analysis

The $H_2O$, sodium, carbon, chloride and metals contents and the specific surface are determined by methods of analysis known to a person skilled in the art. The water content can, for example, be determined by the loss in weight of the catalyst at 100° C. The chloride, sodium and metals contents can be determined by ICP-OES ou ICP-MS. The specific surface is determined by the BET method according to the common practice of a person skilled in the art. The carbon content can be measured according to the standard ASTM D2866. Reference may be made, for example, to the work "Handbook of Heterogeneous Catalysis, Volume 2—Characterization of Solid Catalysts, 2nd Edition" (Wiley-Gerhard Ertl (Editor), Helmut Knözinger (Editor), Ferdi Schüth (Editor), Jens Weitkamp (Editor)), 2008.

Example 1

A tubular stainless steel reactor with an internal diameter of 2.1 cm and a length of 120 cm containing 330 cm$^3$ of catalyst in the form of a fixed bed is used. Throughout the duration of the reaction, approximately 4.2 mol/h of hydrogen (8.4 g/h) and 0.7 mol/h (105 g/h) of hexafluoropropene are continuously injected. The pressure is 2 bara. The hydrogen/HFP molar ratio at the inlet of the reactor is 6. The temperature at the reactor inlet is 39.7° C. and the maximum temperature reached during the reaction is 110.3° C. The contact time following the definition given above is 10.8 s. In this example, two catalysts were tested. The catalyst used in example 1-1 contains 0.2% by weight of Pd/α-alumina and less than 100 ppm of carbon and has a specific surface of >4 m$^2$/g. The catalyst used in example 1-2 contains 0.2% by weight of Pd/α-alumina and 1500 ppm of carbon and has a specific surface >4 m$^2$/g. The results are shown in table 1 below. A 100% conversion of HFP with a selectivity for HFC-236ea of 99.5% is obtained in the presence of a catalyst according to the present invention, versus a selectivity of 98.9% with a catalyst comprising a carbon content of greater than 1500 ppm. In addition, a deactivation of the catalyst used in example 1-2 is observed.

TABLE 1

Results according to example 1

| | Carbon content | Conversion (%) | Selectivity for 236ea (%) |
|---|---|---|---|
| Example 1-1 | <100 ppm | 100 | 99.5 |
| Example 1-2 (comparative) | 1500 ppm | 97.5 | 98.4 |

Example 2

Example 1 is repeated with a catalyst comprising 0.2% by weight of palladium supported on α-alumina, less than 100 ppm of carbon, 50 ppm of sodium and 0.1% by weight of water. A 99.8% conversion of HFP with a selectivity for HFC-236ea of 99.3% is obtained.

The invention claimed is:

1. A catalyst comprising a) from 90% to 99.99% by weight of alumina in which said alumina is at least 90% by weight α-alumina, b) from 0.01% to 10% by weight of at least one metal of valency 0 selected from the group consisting of Pd, Ru, Pt, Rh and Ir, and c) carbon, wherein the carbon content of said catalyst is 10 ppm to 900 ppm, based on the total weight of the catalyst.

2. The catalyst as claimed in claim 1, wherein the water content of said catalyst is less than 2% by weight, based on the total weight of the catalyst.

3. The catalyst as claimed in claim 1, wherein the content by weight of sodium is less than 100 ppm, based on the total weight of the catalyst.

4. The catalyst as claimed in claim 1, wherein the content by weight of antimony is less than 20 ppm, based on the total weight of the catalyst.

5. The catalyst as claimed in claim 1, wherein:
the content by weight of gold is less than 100 ppm, based on the total weight of the catalyst, and/or
the content by weight of lead is less than 50 ppm, based on the total weight of the catalyst, and/or
the content by weight of zinc is less than 250 ppm, based on the total weight of the catalyst, and/or
the content by weight of iron is less than 50 ppm, based on the total weight of the catalyst, and/or
the content by weight of copper is less than 50 ppm, based on the total weight of the catalyst, and/or
the content by weight of magnesium is less than 50 ppm, based on the total weight of the catalyst, and/or
the content by weight of calcium is less than 50 ppm, based on the total weight of the catalyst, and/or
the content by weight of nickel is less than 50 ppm, based on the total weight of the catalyst, and/or
the content by weight of chromium is less than 10 ppm, based on the total weight of the catalyst, and/or
the content by weight of cobalt is less than 10 ppm, based on the total weight of the catalyst, and/or
the content by weight of manganese is less than 10 ppm, based on the total weight of the catalyst.

6. A process for the hydrogenation of an olefin comprising at least one fluorine atom, the process comprising bringing said olefin into contact with hydrogen in the gas phase in the presence of the catalyst as claimed in claim 1, in order to form an alkane compound resulting from the hydrogenation of said olefin.

7. The process as claimed in claim 6, wherein said olefin is selected from the group consisting of 1,1,2,3,3,3-hexafluoropropene, 1,2,3,3,3-pentafluoropropene, 1,1,3,3,3-pentafluoropropene, 1,3,3,3-tetrafluoropropene, 2,3,3,3-tetrafluoropropene, 1,2-dichloro-3,3,3-trifluoropropene, 1-chloro-3,3,3-trifluoropropene and 2-chloro-3,3,3-trifluoropropene.

* * * * *